United States Patent
Cohan et al.

(10) Patent No.: US 10,636,012 B2
(45) Date of Patent: *Apr. 28, 2020

(54) METHODS AND SYSTEMS FOR MANAGING DRUG USAGE

(71) Applicant: Express Scripts Strategic Development, Inc., St. Louis, MO (US)

(72) Inventors: Kevin C. Cohan, Ballwin, MO (US); William G. Fogarty, IV, Florissant, MO (US); Bryan V. Muehlberger, Wildwood, MO (US); Katherine H. Sundaraman, St. Louis, MO (US)

(73) Assignee: Express Scripts Strategic Development, Inc., St. Louis, MO (US)

( * ) Notice: Subject to any disclaimer, the term of this patent is extended or adjusted under 35 U.S.C. 154(b) by 90 days.

This patent is subject to a terminal disclaimer.

(21) Appl. No.: 14/323,477

(22) Filed: Jul. 3, 2014

(65) Prior Publication Data

US 2014/0316803 A1    Oct. 23, 2014

Related U.S. Application Data

(63) Continuation of application No. 13/338,738, filed on Dec. 28, 2011, now Pat. No. 8,799,016.

(51) Int. Cl.
| | | |
|---|---|---|
| *G06Q 10/10* | (2012.01) | |
| *G16H 20/10* | (2018.01) | |
| *A61B 5/00* | (2006.01) | |
| *G06K 9/00* | (2006.01) | |

(52) U.S. Cl.
CPC .......... *G06Q 10/109* (2013.01); *G16H 20/10* (2018.01); *A61B 5/4833* (2013.01); *G06K 9/00* (2013.01)

(58) Field of Classification Search
CPC ...... G06Q 50/22; G06Q 50/24; G06Q 10/087; G06Q 10/00; G06Q 30/00; G06F 19/322–327; G06F 19/3456; G06F 19/3462; G06F 19/3418; G06F 19/326; G06F 21/10; G06F 21/105; G06F 21/12;
(Continued)

(56) References Cited

U.S. PATENT DOCUMENTS 8,799,016 B1 * 8/2014 Cohan ................. G06F 19/3456
705/2
2002/0032583 A1 * 3/2002 Joao ...................... G06F 19/328
705/2
(Continued)

FOREIGN PATENT DOCUMENTS

WO    2010009278 A2    1/2010

*Primary Examiner* — Rachel L. Porter
(74) *Attorney, Agent, or Firm* — Husch Blackwell LLP

(57) ABSTRACT

Methods and systems for managing drug usage are provided. In an embodiment, reminder data associated with a drug treatment plan of a patient is accessed. The reminder data includes a reminder time indicia and a patient identifier associated with the patient. The drug treatment plan is associated with a drug to be taken by the patient. A determination of whether a reminder criterion of the prescription drug treatment plan has been met is made based on the reminder time indicia. A patient messaging configuration is accessed based on the patient identifier. A notification is generated based on a determination that the reminder criterion has been met and the patient messaging configuration. Additional methods and systems are disclosed.

12 Claims, 6 Drawing Sheets

(58) Field of Classification Search
CPC ........ G06F 21/121; G06F 21/30; G06F 21/31;
G06F 21/335; G06F 21/60; G06F 21/629;
G06F 2221/0735; G06F 2221/0771; G06F
2221/2137; G06C 50/22; G06C 50/24;
G16H 10/00; G16H 10/20; G16H 10/40;
G16H 10/60; G16H 10/65; G16H 15/00;
G16H 20/00; G16H 20/10; G16H 20/13;
G16H 20/17; G16H 20/30; G16H 20/40;
G16H 20/60; G16H 20/70; G16H 20/90;
G16H 30/00
See application file for complete search history.

(56) References Cited

U.S. PATENT DOCUMENTS

| | | | |
|---|---|---|---|
| 2003/0099158 A1* | 5/2003 | De la Huerga | A61J 7/0084 |
| | | | 368/10 |
| 2004/0073454 A1* | 4/2004 | Urquhart et al. | 705/2 |
| 2005/0041531 A1 | 2/2005 | Sekura | |
| 2007/0260174 A1 | 11/2007 | Jung et al. | |
| 2008/0126130 A1 | 5/2008 | Miller et al. | |
| 2008/0275738 A1 | 11/2008 | Shillingburg | |
| 2009/0167531 A1* | 7/2009 | Ferguson | G06F 19/3462 |
| | | | 340/572.1 |
| 2012/0101847 A1* | 4/2012 | Johnson | G06Q 10/00 |
| | | | 705/3 |
| 2012/0313785 A1* | 12/2012 | Hanson | G08B 23/00 |
| | | | 340/573.1 |
| 2014/0188502 A1* | 7/2014 | Defrank | G06F 19/3462 |
| | | | 705/2 |

* cited by examiner

METHODS AND SYSTEMS FOR MANAGING DRUG USAGE

CROSS REFERENCE TO RELATED APPLICATION

This application claims priority to and is a continuation of U.S. patent application Ser. No. 13/338,738 filed on Dec. 28, 2011, entitled "METHODS AND SYSTEMS FOR MANAGING DRUG USAGE" the entire disclosure of which is incorporated herein by reference.

FIELD

The field relates to mobile electronic devices, and more particularly to promoting drug plan adherence through the use of mobile electronic devices.

BACKGROUND

Prescription drugs and the drug benefit plans that often provide those drugs have radically improved the health and well-being of vast numbers of people, especially of the older generation. Typically, the use of prescription drugs is controlled by a physician or other care provider who examines a patient to diagnose a disease or other ailment and issues a prescription for a prescription drug. The patient takes the written prescription to a pharmacy where the prescription is filled. If the patient is a member of a drug benefit plan, the patient may not have to pay the usual and customary rate for the prescription drug.

DETAILED DESCRIPTION

Example methods and systems for managing drug usage are described. In the following description, for purposes of explanation, numerous specific details are set forth in order to provide a thorough understanding of example embodiments. It will be evident, however, to one of ordinary skill in the art that embodiments of the invention may be practiced without these specific details.

Generally, prescription drug treatment under a drug benefits plan is facilitated by a pharmacy benefits manager (PBM) for a client. Examples of clients include governmental organizations (e.g., Federal government agencies, the Department of Defense, the Centers for Medicare and Medicaid Services and state government agencies), middle market companies, large national employers, health insurance companies that have carved out the drug benefit, and the like. A person who is a participant or member of the drug benefit plan offered by the client may obtain prescription drugs according to pricing, pharmacy selection, rebates, discounts, and the like provided by the terms of the drug benefit plan. The PBM may be a stand-alone PBM, or may be part of a larger organization that offers other benefits or services.

In some embodiments, the member may be made aware of the need to take the prescription drug or other medication at the appropriate times through the use of a mobile electronic device. Notifications may be provided to a device operator of the mobile electronic device who may be the member that is a participant in the drug benefit plan, a beneficiary of the participant (e.g., a spouse or child of the beneficiary), or who may be another person (e.g., a parent, guardian, caregiver, or the like) operating the mobile electronic device on behalf of the member.

Figure 1:
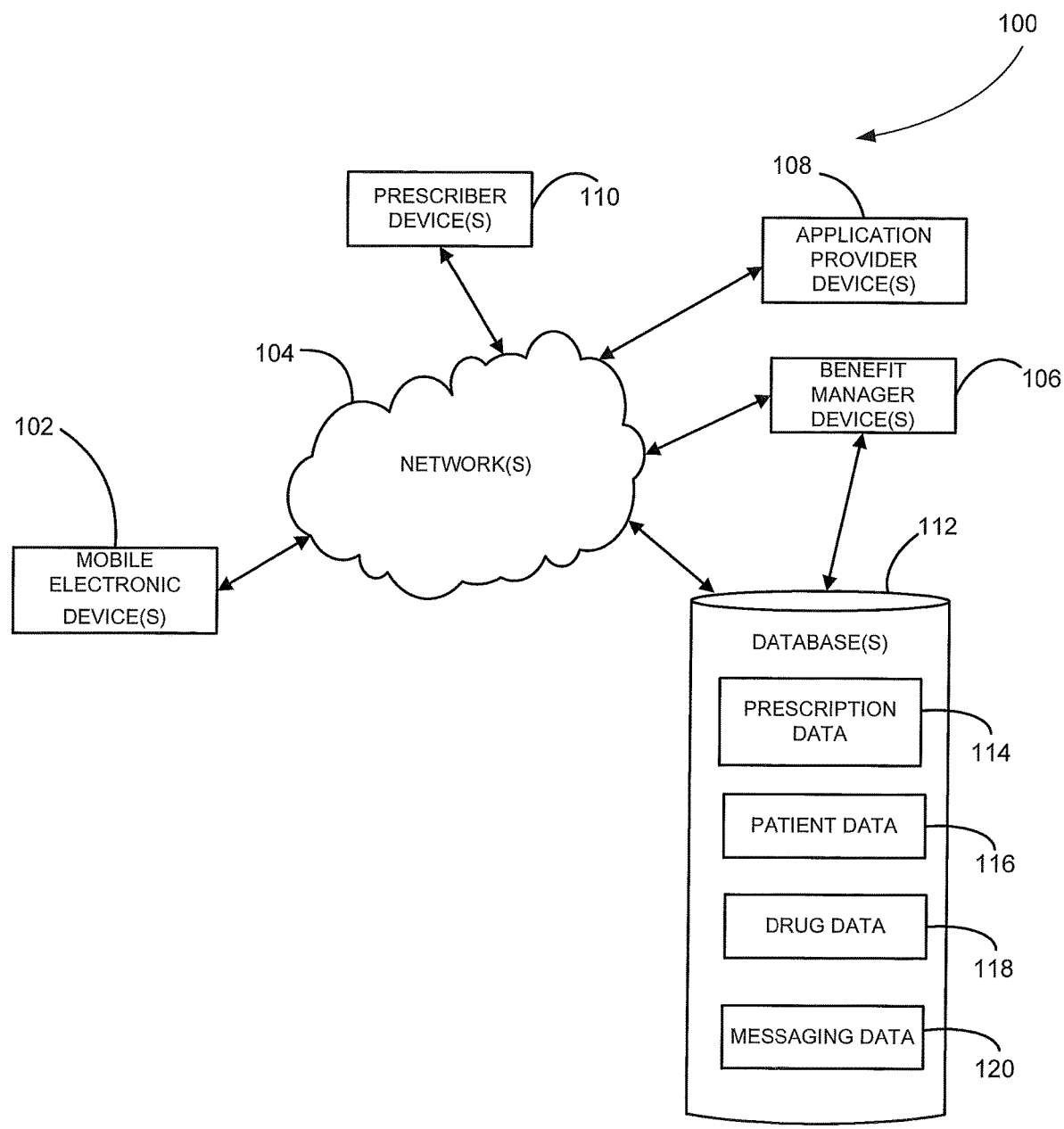
FIG. 1 is a block diagram of an example system, according to an example embodiment.

FIG. 1 is a block diagram of an example system 100, according to an example embodiment. The system 100 is an example environment in which a member, or a person assisting the member, may receive notifications associated with an identifier of a member of a drug treatment plan. The system 100 includes a mobile electronic device 102 in communication with a benefit manager 106 over a network 104.

The mobile electronic device 102 is used by a device operator. The device operator may be a member that is either a participant in a drug benefit plan or a beneficiary of the participant (e.g., a spouse or a child of the beneficiary). However, the device operator may be another person acting on behalf of the member. Examples of such people include parents, guardians, and caregivers. In some embodiments, the device operator may be a patient of a pharmacy (e.g., through a prescribed drug or otherwise), or acting on behalf of a patient of a pharmacy. The patient of the pharmacy may or may not be a member of a drug benefit plan.

The mobile electronic device 102 may be a stand-alone device that solely provides at least some of the functionality to enable management of drug usage, or may be a multi-use device that has functionality outside of drug usage management as described herein. Examples of the mobile electronic device 102 include an IPHONE device by Apple, Inc., mobile electronic devices powered by ANDROID by Google, Inc., and a BLACKBERRY device by Research In Motion Limited. These devices may be capable of receiving instructions, storing instructions, executing instructions, storing the execution results or sending information to a further computing device. Other types of mobile electronic devices may also be used. These can include, but are not limited to, portable computing devices and portable communication devices.

The network 104 by which the mobile electronic device 102 communicates with the benefit manager device 106 may include, by way of example, a Mobile Communications (GSM) network, a code division multiple access (CDMA) network, a 3$^{rd}$ Generation Partnership Project (3GPP) network, an Internet Protocol (IP) network, a Wireless Application Protocol (WAP) network, a WiFi network, or an IEEE 802.11 standards network, as well as various combinations thereof. Network 104 may also include optical communications. Other conventional and/or later developed wired and wireless networks may also be used.

The benefit manager device 106 may be a device operated by an entity at least partially responsible for creation and/or management of the pharmacy benefit plan. While the benefit manager operating the benefit manager device 106 is typically a PBM, other entities may operate the benefit manager device 106 either on behalf of themselves, the PBM, or another entity.

Some of the operations of the PBM that operates the benefit manager device 106 may include the following. A member (or a person on behalf of the member) attempts to obtain a prescription drug at a retail pharmacy location where the member can obtain drugs in a physical store from a pharmacist or pharmacist technician, or in some instances through mail order drug delivery from a mail order pharmacy location. The member may have a co-pay for the prescription drug that reflects an amount of money that the member is responsible to pay the pharmacy for the prescription drug. The money paid by the member to the pharmacy may come from the personal funds of the member, a health savings account (HSA) of the member or the member's family, a health reimbursement arrangement (HRA) of the member or the member's family, a flexible spending accounts (FSA) of the member or the member's family, or the like. An employer of the member may directly or indirectly fund or reimburse the member or an account of the member for the co-pay.

The amount of the co-pay paid by the member may vary by the benefit plan of the client with the PBM. The member's co-pay may be based on or be a flat co-pay (e.g., $10), co-insurance (e.g., 10%), and/or a deductible (e.g., for first $500 of annual prescription drug spending) for certain prescription drugs, certain types of prescription drugs, and/or all prescription drugs.

In certain instances, the member may not pay the co-pay or may only pay for a portion of a co-pay for a prescription drug. For example, if the usual and customary cost for a generic version of a prescription drug is $4, and the member's flat co-pay is $20 for the prescription drug, the member may only pay $4 to receive the prescription drug. In another example involving a worker's compensation claim, no co-pay may be due by the member for the prescription drug.

In conjunction with receiving the co-pay (if any) from the member and dispensing the prescription drug to the member, the pharmacy submits a claim to the PBM for the prescription drug. The PBM may perform certain adjudication functions including verifying the eligibility of the member, reviewing the formulary to determine appropriate co-pay, coinsurance, and deductible for the prescription drug, and performing a drug utilization review (DUR) on the member. The PBM then adjudicates the claim associated with the prescription drug and provides a response to the pharmacy following performance of the aforementioned functions. As part of the adjudication, the client (or the PBM on behalf of the client) ultimately reimburses the pharmacy for filling the prescription drug when the prescription drug was successfully adjudicated. The aforementioned adjudication functions generally occur before the co-pay is received and the prescription drug dispensed. However, the operations may occur simultaneously, substantially simultaneously, or in a different order. In addition, more or less adjudication functions may be performed as part of the adjudication process.

The amount of reimbursement paid to the pharmacy by the client and/or member may be based at least in part on the type of pharmacy network in which the pharmacy is included. Other factors may be used to determine the reimbursement amount in addition to the type of pharmacy network.

The mobile electronic device 102, operating on its own or in combination with the benefit manager device 106, may generate a notification to remind the device operator that either the device operator or another person is to take a dose of a medication. The notification may be provided to the device operator through a display on the mobile electronic device 102, audibly on the mobile electronic device 102, through a different device based upon a transmission from the mobile electronic device 102, or otherwise. Multiple channels may be used to communicate the notification to the device operator and/or non-device operating member.

In some embodiments, a mobile application or app may be downloaded, installed, and launched on the mobile electronic device 102 to enable the management of drug usage. The mobile application may take advantage of hardware and/or software functionality provided by manufactures of the mobile electronic device 102 and/or developers of the operating system of the mobile electronic device 102. For example, the mobile application may use the SAFARI web browser on the IPHONE device, the webkit browser on an ANDROID device, the MOBILE INTERNET EXPLORER on a WINDOWS MOBILE device, or functionality from any of the aforementioned devices. The mobile application may include instructions that when executed on the mobile electronic device 102 or in the benefit manager device 106 cause a machine to change its state or perform tasks within the machine and with other machines. The tasks may take information and change the information to a different output.

The mobile application may be downloaded from an application provider device 108 or directly from the benefit manager device 106. In general, the application provider device 108 is an entity that makes available mobile applications created by the application provider and/or third parties (e.g., the benefit manager) for download and use on mobile electronic devices. Examples of companies that operate the application provider device 108 include Apple, Inc. through its operation of ITUNES STORE, Google, Inc. through its operation of ANDROID MARKET, AT&T through its operation of its APPCENTER, and Research In Motion Limited through its operation of BLACKBERRY APP WORLD. Each of these application provider device companies can host and supply proprietary apps, open apps, and apps by third parties. Updated versions of the mobile applications and/or data to be used by the mobile applications may be provided by the benefit manager device 106, the application provider service 106, or may otherwise be provided.

The mobile electronic device 102 may be in a client-server relationship with the benefit manager device 106 and/or the application provider device 108, a peer-to-peer relationship with the benefit manager device 106 and/or the application provider device 108, or in a different type of relationship with the benefit manager device 106 and/or the application provider device 108.

In general, a prescriber operating a prescriber device 110 is a person that is capable of writing a prescription for a medication. Examples of prescribers include doctors and nurse practitioners. In some embodiments, the prescribers may be part of a physician network. For example, the physician network may be able to obtain legally valid scripts in one or more of the states or other geographic regions. The prescriber may use the prescriber device 110 to review information received about a member (e.g., the device operator) and approve the member to have or otherwise receive an electronic script for a medication (e.g., a prescription drug). In general, the electronic script is for a particular member. However, in some embodiments the electronic script may be for a group of people (e.g., a member and the member's family).

The prescriber device 110 may be associated with a single prescriber, or multiple prescribers. A prescriber may use a single prescriber device or multiple prescriber devices.

The benefit manager device 106 may be in communication directly (e.g., through local storage) and/or through the network 104 (e.g., in a cloud configuration or software as a service) with a database 112. The database 112 may store prescription data 114, patient use data 116, drug data 118 and/or messaging data 120.

The prescription data 114 includes information regarding prescriptions that may be issued by prescribers on behalf of patients, who may be members of the drug benefit plan, for example to be filled by a pharmacy. Examples of the electronic prescription data 114 include patient names, medication or treatment (such as lab tests), dosing information, and the like. The prescriptions may be electronic prescriptions, paper prescriptions that have been scanned, or otherwise. In some embodiments, the dosing information reflects a frequency of use (e.g., once a day, twice a day, before each meal, etc.) and a duration of use (e.g., a few days, a week, a few weeks, a month, etc.)

The patient data 116 includes information regarding patients. In some embodiments, the patient data 116 includes information about the members associated with the benefit manager. Examples of the patient data 116 include name, address, telephone number, e-mail address, prescription drug history, and the like. The patient data 112 may include a client identifier that identifies the client associated with the member and/or a member identifier that identifies the member to the client.

In some embodiments, the patient data 116 includes information on medication use for respective patients and details of drug plan usage. The patient data 116 may include an identifier of the patient, the physician, and of the drug and a time of dosing of the drug. The identifier of the patient may include an image of the patient or another person. The identifier of the drug may include a drug image.

In some embodiments, the patient data 116 includes reminder data that may be used by the patient or a person on behalf of the patient to generation a notification that reminds the patient (directly or through the person on behalf of the patient) to take a dose of the prescription drug or other medicine.

In some embodiments, the patient data 116 includes a patient messaging configuration. The patient messaging configuration may reflect a way, or more than one way, in which a patient desires to receive notifications (e.g., regarding prescription drugs). The way may include a delivery channel (e.g., through the mobile electronic device 102), a delivery type (e.g., visually, audibly, or otherwise), a delivery person (e.g., the patient and/or a person acting on behalf of the patient), or the like.

The drug data 118 may include drug name (e.g., technical name and/or common name), other names by which the drug is known by, active ingredients, an image of the drug (e.g., in pill form), and the like. The drug data 118 may include information associated with a single medication or multiple medications.

The messaging data 120 includes data used to send notifications to a device operator regarding patients. In general, the messaging data 120 may reflect standardized messages used for all members, specific messages for specific patients, and the like.

Certain data from the database 112 may be stored on the mobile electronic device 102 separate from or in addition to the data stored in the database 112. In some embodiments, the data may be stored on the mobile electronic device 102 instead of in the database 112.

While the system 100 in FIG. 1 is shown to include single devices 102, 106, 108, multiple devices may be used. The devices 102, 106, 108 may be the same type of device or may be different device types. When multiple devices are present, the multiple devices may be of the same device type or may be of a different device type. Moreover, system 100 shows a single network; however, multiple networks can be used. The multiple networks may communicate in series with each other to link the devices 102, 106, 108 or in parallel to link the devices 102, 106, 108.

In some embodiments, at least some of the functionality of the application provider device 108 may be included in the benefit manager device 106. In such embodiments, the application may be downloadable directly from the benefit manager device 106 or at the direction of the benefit manager device 106 from the database 112 which may store the application.

Figure 2:
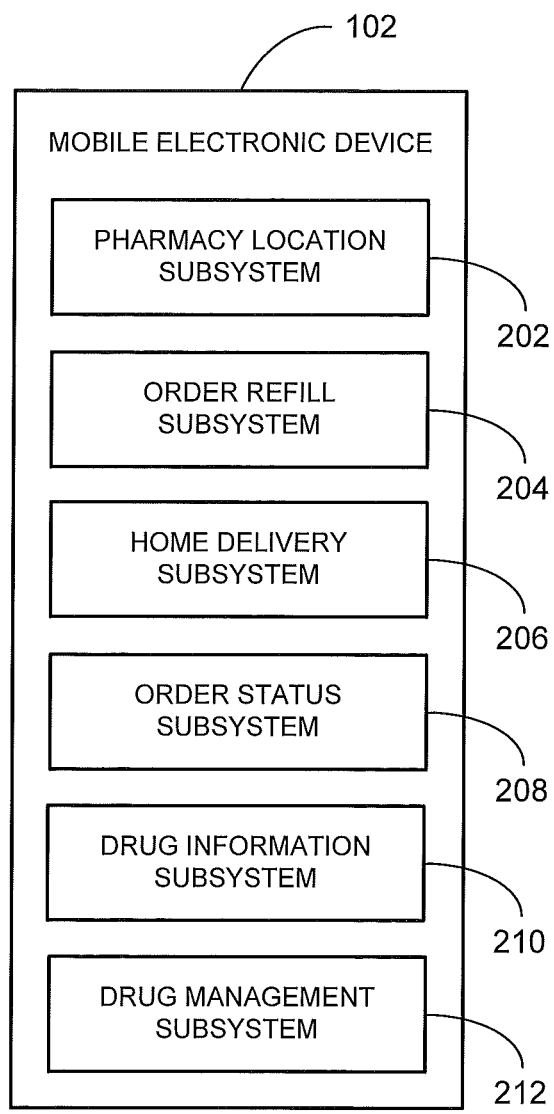
FIG. 2 is a block diagram of an example mobile electronic device that may be deployed within the system of FIG. 1, according to the example embodiment.

FIG. 2 illustrates the mobile electronic device 102, according to an example embodiment. The mobile electronic device 102 may be used by the device operator to manage drug usage. The mobile electronic device 102 may be deployed in the system 100, or may otherwise be used.

The mobile electronic device 102 may include a pharmacy location subsystem 202, an order refill subsystem 204, a home delivery subsystem 206, an order status subsystem 208, a drug information subsystem 210, and/or an drug management subsystem 212.

The pharmacy location subsystem 202 enables the device operator of the mobile electronic device 102 to locate a nearby pharmacy. Examples of nearby pharmacies include the physically or geographically closest pharmacies, pharmacies within a certain distance that have the shortest drive time from the current location of the mobile electronic device 102, a pharmacy with a shortest wait time for prescription fulfillment, or the like.

The order refill subsystem 204 enables the device operator to obtain refills for prescription drugs of the member and/or the member's family. The prescription drugs may have been previously filled at retail, through mail order, or otherwise.

The home delivery subsystem 206 enables the device operator to start home delivery service for prescription drugs. The home delivery service through mail order may be for a single prescription drug or multiple prescriptions drugs of the member and/or the member's family.

The order status subsystem 208 enables the device operator to review the status of orders for prescription drugs. Thus, through the order status subsystem 208, the status of a specific order of a member (e.g., the device operator) and/or the member's family may be reviewed. The status of current orders and/or past orders of the member and/or the member's family may also be available for review.

The drug information subsystem 210 enables the device operator to obtain drug information about prescription drugs. The device operator can interact with the drug information subsystem 210 (e.g., via a user interface) to search by drug name. In addition, the device operator can interact with the drug information subsystem 210 to browse by prescription drug name alphabetically through drug navigation. The provided information on prescription drugs may be information included within the DRUGDIGEST database. This prescription drug data may be stored in the database 110 as at least part of the drug data 118, or may be received through interaction with a different computing device and/or database.

The drug management subsystem 212 enables the device operator to receive notifications regarding the need of the device operator and/or other patients to take a medicine.

Figure 3:
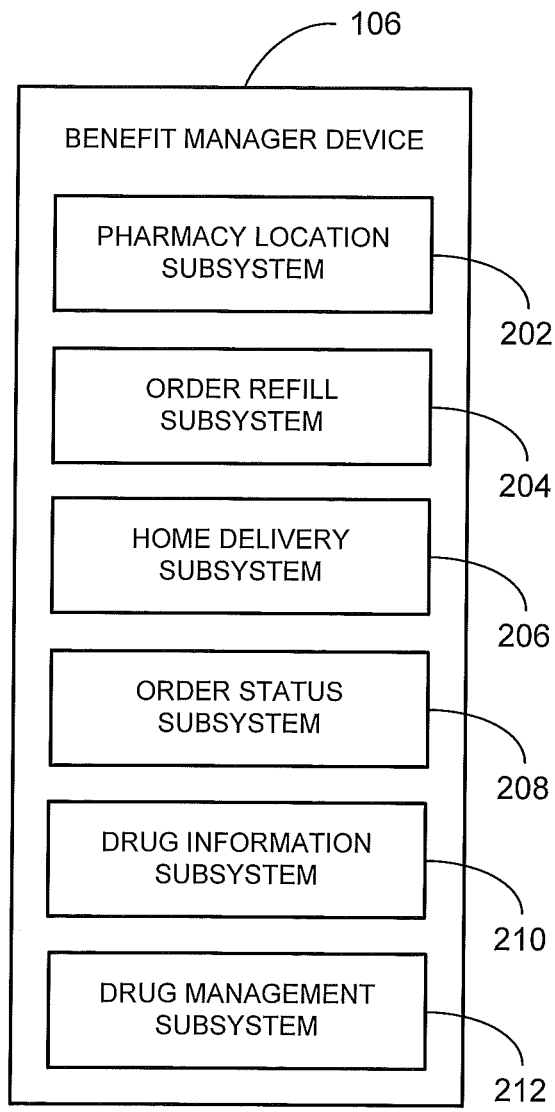
FIG. 3 is a block diagram of an example of a benefit manager device that may be deployed within the system of FIG. 1, according to an example embodiment.

FIG. 3 illustrates the benefit manager device 106, according to an example embodiment. The benefit manager device 106 may be deployed in the system 100, or may otherwise be used.

The benefit manager device 106 may include the pharmacy location subsystem 202, the order refill subsystem 204, the home delivery subsystem 206, the order status subsystem 208, the drug information subsystem 210 and/or the drug management subsystem 212. In some embodiments, one or more of the various subsystems 202-212 when used may provide server-side functionality to the mobile electronic device 102. By way of example, the awareness subsystem 202 may be deployed in both the mobile electronic device 102 and the benefit manager device 106. The mobile electronic device 102 may then perform some of the functionality while other functionality is performed by the benefit manager device 106.

Figure 4:
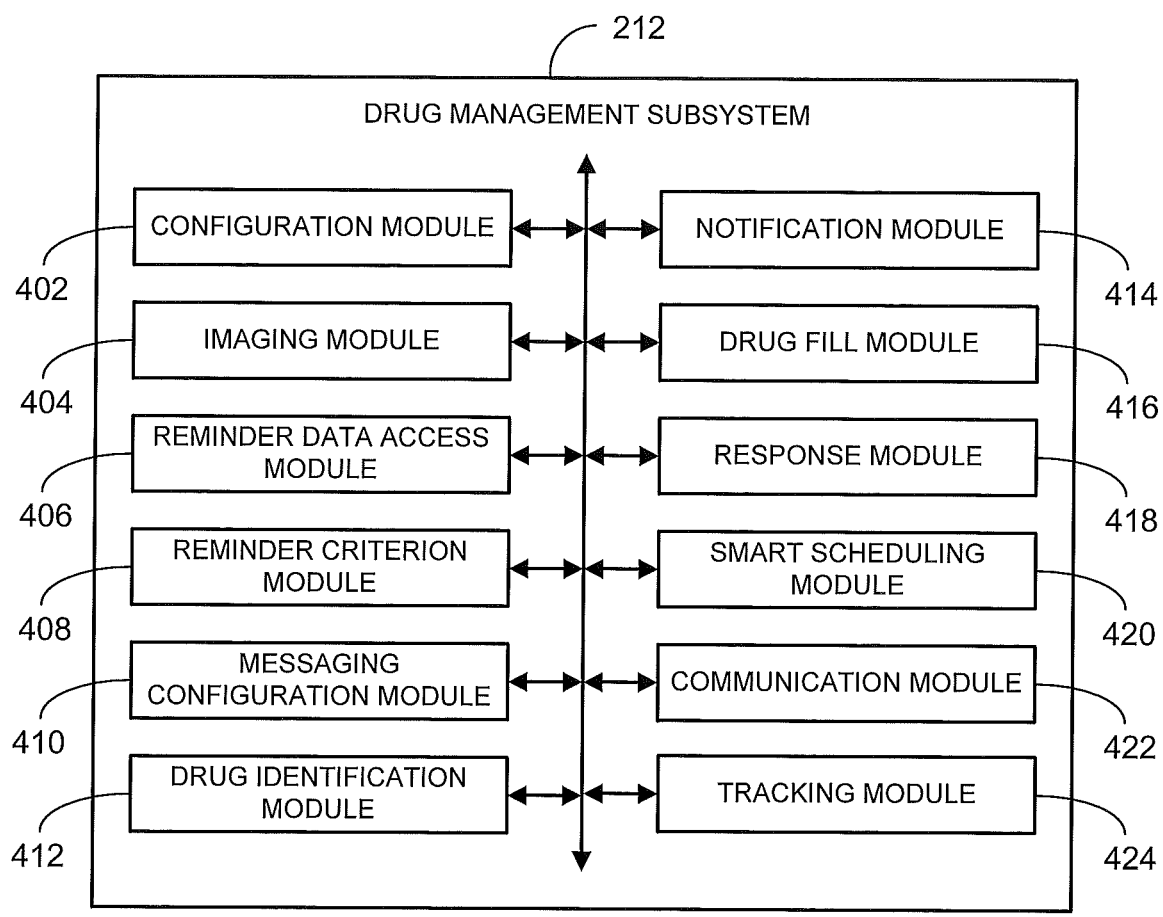
FIG. 4 is a block diagram of an example of a drug management subsystem that may be deployed within the mobile electronic device of FIG. 2 or the benefit manager device of FIG. 3, according to an example embodiment.

FIG. 4 illustrates the drug management subsystem 212 that may be deployed in the mobile electronic device 102, the benefit manager device 106, or otherwise deployed in another system. One or more modules are communicatively coupled and included in the drug management subsystem 212 to enable management of prescription and/or non-prescription drugs. The modules of the drug management subsystem 212 that may be included are a configuration module 402, an imaging module 404, a reminder data access module 406, a reminder criterion module 408, a messaging configuration module 410, a drug identification module 412, a notification module 414, a drug fill module 416, a response module 418, a smart scheduling module 420, a communication module 422, and/or a tracking module 424. Other modules may also be included.

In some embodiments, the modules of the drug management subsystem 212 may be distributed so that some of the modules are deployed in the mobile electronic device 102 and some of the modules are deployed in the benefit manager device 106. In one embodiment, the modules are deployed in memory and executed by a processor coupled to the memory. The functionality contained within the modules 402-424 may be combined into a less number of modules, further divided among a greater number of modules, or redistributed among existing modules. Other configurations including the functionality of modules 402-424 may be used.

The configuration module 402 facilitates the set up of the drug management subsystem 212 for managing drug usage. In some embodiments, the drug management subsystem 212, through use of the configuration module 402, may operate in a first mode that only saves the patient data 116 related to drug plan adherence locally on the mobile electronic device 102. In some embodiments, the drug management subsystem 212, through use of the configuration module 402, may operate in a first mode pending identification of the patient and, upon identifying the patient, revert to a second mode where data on drug plan adherence is saved in the patient data 116 in the database 112. In some embodiments, the device operator may enter a system identifier of a website (e.g., an IP address) and download the drug management subsystem 212 in the form of a stand-alone application for saving the patient data 116 relating to plan adherence data locally.

In some embodiments, the imaging module 404 is included within the drug management subsystem 212 deployed on the on the mobile electronic device 102. The imaging module 404 may capture an image of an outside (or inside) surface of a container or packaging (e.g., on a prescription label) that contains the prescription drug. For example, camera functionality included within or otherwise associated with the imaging module 404 may capture a bar code, QR code, or the like from the container. In some embodiments, the configuration module 402 may prompt the device operator for prescription information including a patient identifier associated with the patient, a physician identifier associated with the physician that prescribed or otherwise recommended the drug, a drug identifier associated with the drug, and reminder data indicating when the drug is to be taken by the patient.

In some embodiments, the member may take a digital picture or video clip of a pharmacy prescription label on a bottle of prescription drugs using the imaging module 404. In such embodiments, the mobile electronic device 102 may capture an electronic image of the pharmacy prescription label on the bottle of prescription drugs, in which the electronic image includes a representation of the source pharmacy prescription data (e.g., which may include a barcode, a plain text numeric string, or the like).

The reminder data access module 406 accesses reminder data associated with a drug treatment plan of a patient. The reminder data includes reminder time indicia and a patient identifier associated with the patient. The drug treatment plan is associated with a drug to be taken by the patient. In some embodiments, the reminder time indicia is associated with a drug to be taken by the patient in accordance with a drug treatment plan.

In some embodiments, the reminder data access module 406 provides access to reminder data from a profile associated with a drug treatment plan of a patient. The profile generally reflects the characteristics of a single patient. In some embodiments, the reminder data access module 406 retrieves the prescription data 114 and processes the information into reminder data for a patient.

The reminder criterion module 408 determines whether a reminder criterion of the prescription drug treatment plan has been met based on the reminder time indicia. In general, the reminder criterion reflects a basis of when the device operator should receive a notification associated with a drug while the reminder time indicia reflects a timing of when the device operator should receive the notification. In some embodiments, the reminder criterion reflects a time at which a notification should be provided and the reminder time indicia reflects a current time (e.g., a current time associated with the mobile electronic device 102 and/or the benefit manager device 106). However, the reminder time indicia may reflect a time that would not otherwise be considered a current time such as the time associated with a time zone, a time that is set in advance or behind, or otherwise.

In some embodiments, the reminder criterion may be compared by the reminder criterion module 408 against a time associated with the mobile electronic device 102, which may be a current time, a time zone in which the device operator or a member is based, an absolute time, or a different time. The reminder criterion may include that the time associated with the mobile electronic device 102 is past a reminder time, is within a time period of the reminder time, or the like.

The reminder criterion module 408 may operate on a 7-day a week, 24 hour time basis similar to a clock. The reminder criterion module 408 may also automatically adjust to different time zones. In other example embodiments, the reminder criterion module 408 may simply measure absolute time in hours and fractions thereof from some initialization time or from some repeating event (e.g., midnight).

The messaging configuration module 410 accesses a patient messaging configuration based on the patient identifier.

The drug identification module 412 accesses information about the drug from the reminder data access module 406 and accesses data about the drug from the drug data 118. In some embodiments, the accessed data may be transmitted to the mobile electronic device 102. In an example embodiment, the transmitted data may include an image of the drug.

The notification module 414 generates a notification regarding drug usage. In some embodiments, the notification is generated based on a determination that the reminder criterion has been met and based on the patient messaging configuration. In some embodiments, the notification module 414 receives information from the reminder data access module 406, accesses patient messaging configurations and generates notifications for the patient to take the drug in accordance with the drug treatment plan.

In some embodiments, the notification module 414 generates a notification based on a determination that the reminder criterion has been met and based on the patient messaging configuration. In this regard, the notification module 414 may obtain a patient messaging configuration based on the patient identifier. In some embodiments, the patient messaging configuration includes a display that is generated for presentation on a display device of the mobile electronic device 102. The display may include an identifier of the patient and an identifier of the drug.

In some embodiments, the notification module 414 accesses the prescription drug treatment plan of the patient (e.g., from the prescription data 114 in the database 112) and/or a drug image associated with a drug based upon a patient identifier and a drug identifier.

In an example embodiment, the generating of notifications by the notification module 414 includes processing reminder data from respective drug treatment plan of any number of patients and providing the notification to the mobile electronic device 102 of the device operator associated with the respective patients based upon a patient messaging configuration and a determination that the respective reminder criterion has been met. The reminder criterion module 408 determines whether a reminder criterion of the prescription drug treatment plan has been met based on the reminder time indicia, the messaging configuration module 410 accesses a patient messaging configuration based on the patient identifier and the notification module 414 generates a notification based on a determination that the reminder criterion has been met and on the patient messaging configuration.

In an example embodiment, the messaging configuration module 410 retrieves a patient preference and the notification module 414 generates the notification from the patient preference. The patient preference may specify the mobile electronic device 102 or other communication device associated with the patient or, as applicable, a different device operator. The notification module may then transmit the notification to the mobile electronic device 102 or other communication device specified by the patient preference. A single mobile electronic device 102 or multiple mobile electronic devices may be specified based on the patient preferences. A single other communication device or multiple other communication devices may be specified based on the patient preferences. The other communication devices may include through a set-top box of a television, a telephone through an automated or voice call, or otherwise.

In some example embodiments, the notification module 414 may transmit the notification to the mobile electronic device 102 of a caregiver of a patient and to another device associated with the patient. The sending the notifications by the notification module 414 may occur simultaneously, sequentially, or otherwise.

In some embodiments, the notification module 414 may transmit the notification to a first device or first set of devices, delay transmission of the notification to a second device or second set of devices for a period of time (e.g., a predetermined time period) pending receipt of verification of use through the first device or first set of devices and delivering the notification to the second device or second set of devices upon failure of receipt and/or use by the first device or first set of devices. In some embodiments, instead of or in addition to the second device or second set of devices, the notification may be provided (e.g., transmitted) to an emergency response service.

The notifications generated by the notification module 414 may include a simple reminder to take the drug including a patient identifier associated with the patient and a drug identifier associated with the drug. In some embodiments, the generated notification may include a patient identifier associated with the patient and the drug identifying indicia. In some embodiments, the generated notification may include at least an image of the patient as the patient identifier and an image of the drug as the drug identifying indicia. In some embodiments, the patient identifier includes a sound. In embodiments where the mobile electronic device 102 is being used for multiple patients, a different sound for each patient may be used based on the patient messaging configuration.

In some example embodiments, a drug fill module 416 may detect a refill of a prescription for the drug. The drug fill module may access (e.g., download) a new image of the drug. The new image of the drug may be used by the notification module 414 in generation of the notification. In some embodiments, the notification may include simultaneously displaying an image of the drug from a previous fill of the prescription and the new image of the refill of the prescription. The simultaneous display notification may, in some embodiments, be used for a period of time following the refill. The period of time may be based on a set time period (e.g., 2 days), a number of notifications received regarding the drug (e.g., 5 notifications), or otherwise.

In some embodiments, the notifications may include a request for confirmation of use of the drug in accordance with the drug treatment plan, thereby verifying use of the drug by the patient. The response module 418 may receive confirmation of the drug treatment plan of the patient and store the reminder data based on receipt of confirmation of the drug treatment plan of the patient.

In some embodiments, the response module 418 receives identification of the patient, a reminder time schedule associated with the drug treatment plan, and identification of the drug and generates a confirmation request display based on receipt of the identification of the patient, the reminder time schedule associated with the drug treatment plan, and the identification of the drug. The confirmation received by the response module 418 may then be in response to generation of the display.

In some embodiments, the response module 418 may receive an electronic image of a drug label associated with the drug (e.g., from the imaging module 404) and determine the patient, the reminder time schedule associated with the drug treatment plan, and identification of the drug based on the drug label.

In some example embodiments, confirmation by the response module 418 may include a multistep confirmation process where the drug is identified and the device operator is requested to identify the drug to be given to the patient. If the proposed drug identifier sent by the notification module 414 to the device operator matches the drug identifier received from the device operator, then the notification module 414 authorizes use of the drug and requests confirmation of such use. The notification module 414 reports confirmation of use to the response module 418. In this case, confirmation may include receiving verification of use of the drug by the patient in accordance with the treatment plan and saving the received verification. Confirmation may also include receiving an electronic image of a drug label associated with the drug, determining the drug corresponds to the drug label, and authorizing the patient to consume the drug.

The smart scheduling module 420 detects acknowledgements of use of a drug under a drug treatment plan from the notification module 414 and compares a time of use with the time requirements of the drug treatment plan. Where the time of use deviates from the use suggested by the drug treatment plan, the smart scheduling module 420 may propose changes in a time of use or automatically change a time of use. For example, the verification of use of the drug by the patient may be received by the response module 418 in accordance with the treatment plan and saved by the response module 418. In some embodiments, the response module 418 may receive verification of use of the drug by the patient under the treatment plan from the mobile electronic device 102, and the smart scheduling module 420 may compare the verifications of use with the reminder criterion and dynamically adjust the reminder time indicia based upon deviations from the reminder time criterion. In some embodiments, the smart scheduling module 420 may access a scheduling calendar associated with the patient and adjust the reminder time indicia to an alternate time based upon preexisting scheduling conflicts identified within the scheduling calendar.

The smart scheduling module 420 may also compare current times of use of the drug with a scheduling system or calendar (e.g., OUTLOOK) of the device operator or patient and propose changes based upon conflicting pre-scheduled events. For example, if the drug is always taken late on weekends or on some repeating day of the week (e.g., Tuesdays) where the patient has a scheduled function (e.g., physical therapy), then the smart scheduling module 420 changes the time of notification on weekends or on the day of the scheduled function.

The smart scheduling module 420 may also receive deviations in drug plan adherence from the response module 418 and from a calendar feature (a calendar device) of the patient (e.g., OUTLOOK, Gmail, etc.). In this case, the smart scheduling module 420 receives notifications of past deviations from the response module 418 and indications of future appointments or commitments from the calendar feature and dynamically changes the reminder data accordingly. For example, if the patient consistently confirms use of the drug at 7 a.m. on weekday mornings, but does not confirm use of the drug on weekends until 8 a.m., then the smart scheduling module 420 may adjust the reminder data to provide a notification at 8 a.m. on weekends and 7 a.m. on weekdays. In some embodiments, when the smart scheduling module 420 detects from the calendar feature that the patient will be on vacation for the next week, then the smart scheduling module 420 may defer reminders until 8 a.m. on all days during the scheduled period of vacation.

Similarly, the patient may alternate between working a night shift for two weeks and then go to a day shift for two weeks. In this case, the smart scheduling module 420 may detect the reversal of confirmation times between the two shift schedules and automatically and proactively adjust the reminder data accordingly.

The communication module 422 may collect data regarding interactions from the device operator on use of the drug under the prescription plan from the notification module 414. The collected data may be saved locally until the patient can be identified and then saved in the database 112.

The communication module 422 may provide rewards to a patient for compliance with the drug treatment plan. In the case of adults, the rewards may be a free ring tone or a discount on the next prescription. In the case of a child, the reward may be a smiley face. Other types of rewards may also be provided.

The communication module 422 may also receive deviations in the time of receipt of confirmation of use and the time of notifications and reward the patient accordingly. For example, if the patient takes the prescribed drug within some minimum threshold time period (e.g., 15 minutes) of the time of the notification over some extended time period (e.g., one week, one month, etc.), then the communication module 422 may bestow some premium on the patient. For an adult, the bestowed premium may be some monetary or material benefit (e.g., a discount on the next prescription refill, a free ring tone, etc.). Similarly, for a child, the bestowed premium may be in the form of encouragement (e.g., a smiley face) provided on a display of the mobile electronic device 102.

The communication module 422 may pose a question to the patient or device operator. A single question or multiple questions may be provided to the patient or device operator. For example, the communication module 422 may operate in conjunction with the smart scheduling module 420 to inquire as to why a deviation occurred between the time of use of the drug under the prescription drug plan and an actual time of use by the patient. In some embodiments, the communication module 422 may inquire about the effects of the drug by asking the patient how taking the drug makes the patient feel. In some embodiments, the communication module 422 determines use of the drug by the patient at a time that deviates from the drug treatment plan, stores the determined deviation, and poses a question to the patient. In some embodiments, the posed question may include querying the patient about why the deviation has occurred. In still other example embodiments, the communication module 422 determines use of the drug in compliance with the drug treatment plan, saves the determined compliance, and poses a question to the patient.

The communication module 422 may pose unrelated questions in order to collect survey data. In such embodiments, the communication module 422 may pose a question along with two or more possible answers. The communication module 422 may process responses in order to indentify the selected one of the offered possible answers.

The communication module 422 may pose questions to the patient. The questions may be posed based upon deviations of greater than the minimum threshold time between receipt of a notification to take the drug and receipt of confirmation of taking the drug or upon other factors. In some embodiments, the communication module 422 may pose questions related to the effect of the drug (e.g., "how does your medication make you feel") to the patient. In some embodiments, the communication module 422 may pose a more direct question (e.g., "why were you late in taking your medication") to the patient.

In other example embodiments, the communication module 422 may pose questions based upon various factors. For example, the communication module 422 may pose questions requesting survey information or questions related to the methods and systems itself. For example, the communication module 422 may pose the question "are our reminders helpful" or "how could our reminders be improved" to the patient.

In some embodiments, the tracking module 424 receives patient information regarding applicable side-effects for medicines that the patient is taking. In some embodiments, the applicable effects module may generate a display that is presented to the device operator that includes known side-effects associated with the medicine. Through a user interface or otherwise, the device operator may select applicable side effects, manually enter side effects, or may otherwise indicate applicable side effects. The side effects data may be stored in the database 118, communicated to the benefit manager device 106 and/or the prescriber device 110, or may otherwise be used.

In some embodiments, the tracking module 424 may collect tracking information about the patient. For example, the activity of the device operator may be tracked directly from a locating device (e.g., a GPS) carried by the mobile electronic device 102, from a motion detection device (e.g., a pedometer) carried by the mobile electronic device 102, or from the activities of the device that can otherwise be detected through use of functionality in the system 100. In the case of the locating device or motion detection device carried by the mobile electronic device 102, the tracking module 424 may periodically retrieve a location or activity level of the device operator and save the location within the patient data 116.

Figure 5:
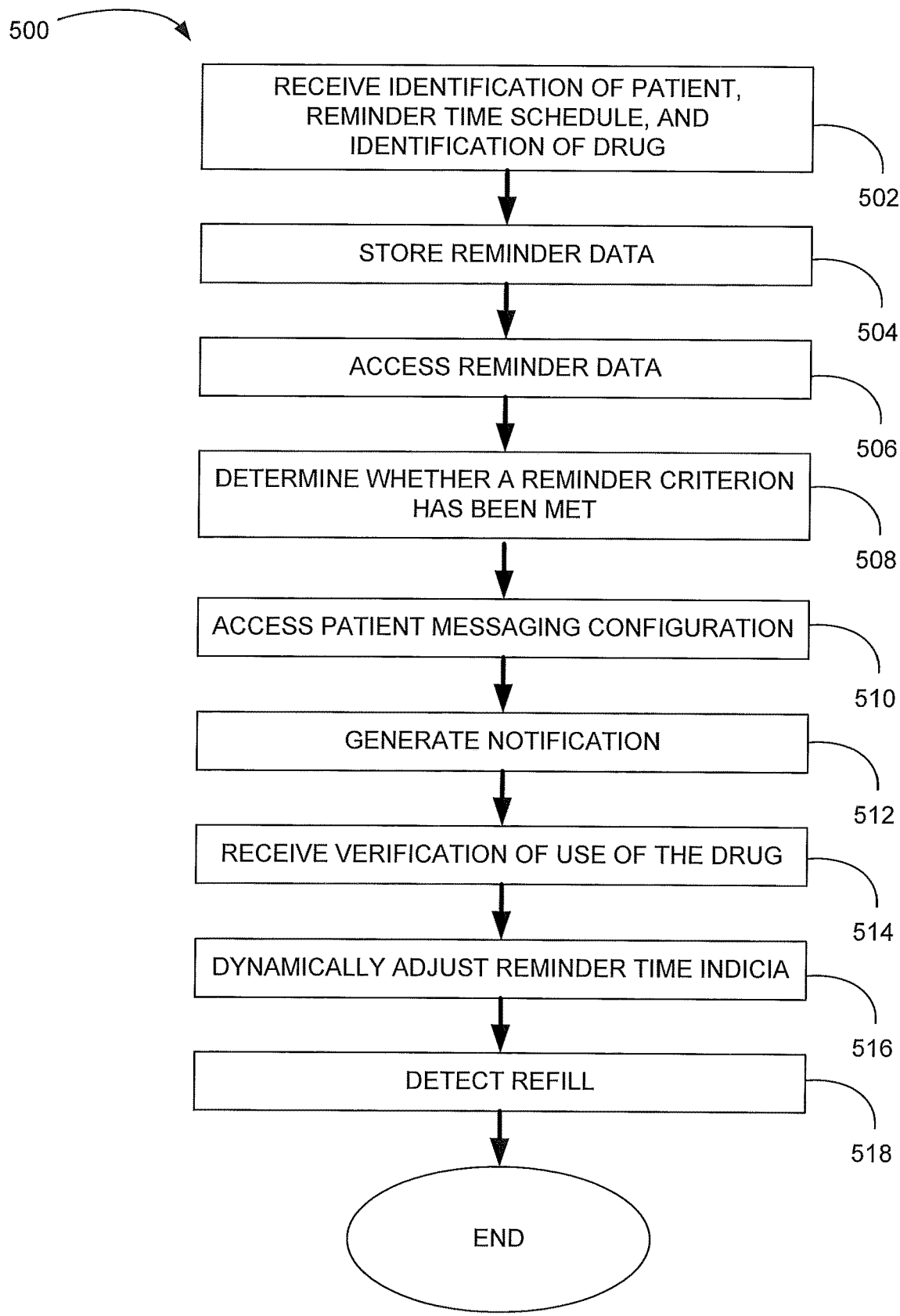
FIG. 5 is a process flow illustrating a method for managing drug use with a prescription drug treatment plan, according to an example embodiment.

FIG. 5 illustrates a method 500 for managing drug usage, according to an example embodiment. The method 500 may be performed by the mobile electronic device 102, by the benefit manager device 106, partially by the mobile electronic device 102 and partially be the benefit manager device 106, or may be otherwise performed.

An identification of the patient, a reminder time schedule and an identification of a drug being taken by the patient may be received at block 502. For example, in some embodiments, camera functionality included within the mobile electronic device 102 may be utilized to capture an electronic image of a drug label included on a container or packaging of the prescription drug. The electronic image may be decoded to determine the identification of the patient, a reminder time schedule (e.g., which may include an indication of when the drug is to be taken by the patient, and identification of the drug associated with the drug label, or any combination of the foregoing. In some embodiments, one, or more than one, of the identification of the patient, the reminder time schedule, and the identification of the drug may be received based on an input made by the device operator of the mobile electronic device 102.

The reminder data associated with a drug treatment plan of the patient may be stored at block 504. The reminder data includes the reminder time indicia, the patient identifier associated with the patient, and the drug treatment plan associated with the drug to be taken by the patient. In some embodiments, the reminder time indicia is associated with a drug to be taken by the patient in accordance with a drug treatment plan.

The reminder data associated with the drug treatment plan of the patient is accessed at block 506. In some embodiments, accessing the reminder data may include accessing the stored remaindered data, e.g., that was determined based on the electronic image of the drug label and/or based on the input made by the device operator of the mobile electronic device 102. In some embodiments, accessing the reminder data may include accessing the reminder data from a profile associated with the drug treatment plan of the patient. The profile may generally reflect the characteristics of a single patient. In some embodiments, accessing the reminder data may include retrieving the prescription data 114 and processing the information from the prescription data and processing the prescription data into the reminder data for the patient.

It may be determined whether a reminder criterion has been met at block 508. Determining whether the reminder criterion has been met may be based on the reminder time indicia. In general, the reminder criterion reflects a basis of when the device operator should receive a notification associated with a drug while the reminder time indicia reflects a timing of when the device operator should receive the notification. In some embodiments, the reminder criterion reflects a time on which a notification should be provided and the reminder time indicia reflects a current time (e.g., a current time associated with the mobile electronic device 102 and/or the benefit manager device 106). However, the reminder time indicia may reflect a time that would not otherwise be considered a current time such as the time associated with a time zone, a time that is set in advance or behind, or otherwise.

In some embodiments, determining whether the reminder time criterion has been met may include comparing the reminder criterion against a time associated with the mobile electronic device 102, which may be a current time, a time zone in which the device operator or a member is based, an absolute time, or a different time. The reminder criterion may include that the time associated with the mobile electronic device 102 is past a reminder time, is within a time period of the reminder time, or the like.

A patient messaging configuration may be accessed at block 510. In some embodiments, accessing the patient messaging configuration may include accessing the patient data 116 from the database 112. In general, the patient messaging configuration may, the patient messaging configuration may reflect a way in which a patient desires to receive notifications (e.g., regarding prescription drugs). The way the patient desires to receive notifications may include a delivery channel (e.g., through the mobile electronic device 102), a delivery type (e.g., visually, audibly, or otherwise), a delivery person (e.g., the patient and/or a person acting on behalf of the patient), or the like.

A notification regarding drug usage may be generated at block 512. The notification may be generated based on the determination that the reminder criterion has been met and based on the accessed patient messaging configuration. In an example embodiment, generating notifications includes processing reminder data from a respective drug treatment plan of any number of patients and providing the notification to the mobile electronic device 102 of the device operator associated with the respective patients based upon a patient messaging configuration and based on a determination that the respective reminder criterion has been met.

In an example embodiment, the notification may be generated based on the patient preference included within the patient messaging configuration. The patient preference may specify that the notification should be transmitted to the mobile electronic device 102 or other communication device associated with the patient or, as applicable, a different device operator. The notification may be transmitted to the mobile electronic device 102 or other communication device specified by the patient preference. A single mobile electronic device 102 or multiple mobile electronic devices may be specified based on the patient preferences. A single other communication device or multiple other communication devices may be specified based on the patient preferences. The other communication devices may include through a set-top box of a television, a telephone through an automated or voice call, or otherwise.

In some example embodiments, notifications may be transmitted to the mobile electronic device 102 of a caregiver of a patient and to another device associated with the patient. Transmitting the notifications may occur simultaneously, sequentially, or otherwise. For example, in some embodiments, the notification may be transmitted to a first device or first set of devices. The notification transmitted to a second device or second set of devices may be delayed for a period of time (e.g., a predetermined time period) pending receipt of verification of use through the first device or first set of devices. The notification may be transmitted to the second device or second set of devices upon failure of receipt and/or use by the first device or first set of devices. In some embodiments, instead of or in addition to the second device or second set of devices, the notification may be provided (e.g., transmitted) to an emergency response service.

A verification of use of the drug may be received at block 514. For example, in some embodiments, the generated notification may request a confirmation of use of the drug by the patient. In such an embodiment, a verification of use of the drug by the patient in accordance with the treatment plan may be received and the received verification may be saved.

The reminder time indicia may be dynamically adjusted at block 516. For example, in some embodiments, verifications of use of a drug under a drug treatment plan may be compared with the time requirements of the drug treatment plan. Where the time of use deviates from the use suggested by the drug treatment plan, changes in a time of use may be proposed or a time of use may be automatically changed. For example, the verification of use of the drug by the patient may be received in accordance with the treatment plan and may be saved. In some embodiments, the verifications of use may be compared with the reminder criterion and the reminder time indicia may be dynamically adjusted based upon deviations from the reminder time criterion. In some embodiments, dynamically adjusting the reminder time indicia may include accessing a scheduling calendar associated with the patient and adjusting the reminder time indicia (and/or proposing an adjustment to the reminder time indicia) to an alternate time based upon preexisting scheduling conflicts identified within the scheduling calendar. In some embodiments, dynamically adjusting the reminder time indicia may be based on repeated deviations from the reminder time criterion having a discernable pattern. For example, the reminder time indicia may be dynamically adjusted based on a pattern of received verifications of use of the drug at 7 a.m. on weekday mornings, but of 8 a.m. on weekend morning, such that the reminder data may provide a notification of 8 a.m. on weekend mornings and of 7 a.m. on weekday mornings. Other adjustments may similarly be made.

A refill of the prescription for the drug may be detected at block 518. In some embodiments, a new image of the drug may be accessed in response to detecting a refill of the prescription drug. In some embodiments, the new image of the drug may be used in connection with notifications generated based on a determination that a reminder criterion has been met. For example, in some embodiments, the notification may include simultaneously displaying an image of the drug from a previous fill of the prescription and the new image of the refill of the prescription. The simultaneous display notification may, in some embodiments, be used for a period of time following the refill. The period of time may be based on a set time period (e.g., 2 days), a number of notifications received regarding the drug (e.g., 5 notifications), or otherwise.

Figure 6:
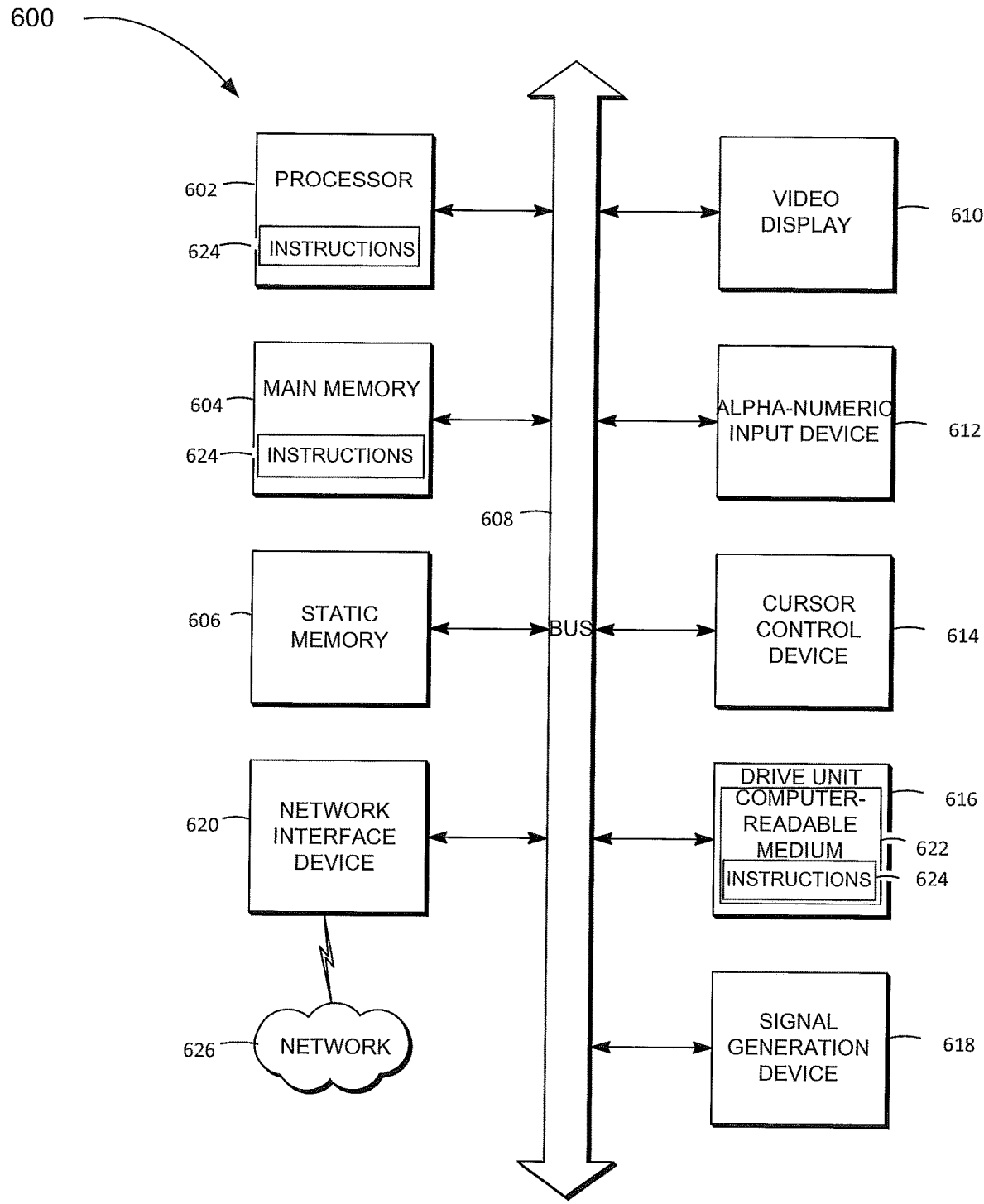
FIG. 6 is a block diagram of a machine in the example form of a computer system within which a set of instructions for causing the machine to perform any one or more of the methodologies discussed herein may be executed or stored.

FIG. 6 shows a block diagram of a machine in the example form of a computer system 600 within which a set of instructions may be executed causing the machine to perform any one or more of the methods, processes, operations, or methodologies discussed herein. The mobile electronic device 102, the benefit manager device 106, and/or the application provider device 108 may include the functionality of the one or more computer systems 600.

In an example embodiment, the machine operates as a standalone device or may be connected (e.g., networked) to other machines. In a networked deployment, the machine may operate in the capacity of a server or a client machine in server-client network environment, or as a peer machine in a peer-to-peer (or distributed) network environment. The machine may be a server computer, a client computer, a personal computer (PC), a tablet PC, a gaming device, a set-top box (STB), a Personal Digital Assistant (PDA), a cellular telephone, a web appliance, a network router, switch or bridge, or any machine capable of executing a set of instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

The example computer system 600 includes a processor 602 (e.g., a central processing unit (CPU) a graphics processing unit (GPU) or both), a main memory 604 and a static memory 606, which communicate with each other via a bus 608. The computer system 600 further includes a video display unit 610 (e.g., a liquid crystal display (LCD) or a cathode ray tube (CRT)). The computer system 600 also includes an alphanumeric input device 612 (e.g., a keyboard), a cursor control device 614 (e.g., a mouse), a drive unit 616, a signal generation device 618 (e.g., a speaker) and a network interface device 620.

The drive unit 616 includes a computer-readable medium 622 on which is stored one or more sets of instructions (e.g., software 624) embodying any one or more of the methodologies or functions described herein. The software 624 may also reside, completely or at least partially, within the main memory 604 and/or within the processor 602 during execution thereof by the computer system 600, the main memory 604 and the processor 602 also constituting computer-readable media.

The software 624 may further be transmitted or received over a network 626 via the network interface device 620.

While the computer-readable medium 622 is shown in an example embodiment to be a single medium, the term "computer-readable medium" should be taken to include a single medium or multiple media (e.g., a centralized or distributed database, and/or associated caches and servers) that store the one or more sets of instructions. The term "computer-readable medium" shall also be taken to include any medium that is capable of storing or encoding a set of instructions for execution by the machine and that cause the machine to perform any one or more of the methodologies of the present invention. The term "computer-readable medium" shall accordingly be taken to include, but not be limited to, solid-state memories, and optical media, and magnetic media. In some embodiments, the computer-readable medium is a non-transitory computer-readable medium.

The term "based on" or using, as used herein, reflects an open-ended term that can reflect others elements beyond those explicitly recited.

Certain systems, apparatus, applications or processes are described herein as including a number of modules. A module may be a unit of distinct functionality that may be presented in software, hardware, or combinations thereof. When the functionality of a module is performed in any part through software, the module includes a computer-readable medium. The modules may be regarded as being communicatively coupled.

The inventive subject matter may be represented in a variety of different embodiments of which there are many possible permutations.

In an embodiment, reminder data associated with a drug treatment plan of a patient is accessed. The reminder data includes a reminder time indicia and a patient identifier associated with the patient. The drug treatment plan is associated with a drug to be taken by the patient. A determination of whether a reminder criterion of the prescription drug treatment plan has been met is made based on the reminder time indicia. A patient messaging configuration is accessed based on the patient identifier. A notification is generated based on a determination that the reminder criterion has been met and the patient messaging configuration.

While the present disclosure in some embodiments refers to prescription drugs and pharmacy benefits, the present disclosure is not so limited. Instead of or in addition to the benefit manager, other types of health plans may be at least partially associated with the generation of the benefit notification. For example, a method may include accessing any drug use profile associated with a mobile electronic device, determining that a reminder time indicia associated with the profile has been met, and generating a drug use notification. Other health care and non-health care organizations may utilize the methods and systems to generate notifications. The methods and systems may also be used to generate notifications in applications involving non-human drug treatments.

Thus, methods and systems for managing prescription drug usage have been described. Although embodiments of the present invention have been described with reference to specific example embodiments, it will be evident that various modifications and changes may be made to these embodiments without departing from the broader spirit and scope of the embodiments of the invention. Accordingly, the specification and drawings are to be regarded in an illustrative rather than a restrictive sense.

The methods described herein do not have to be executed in the order described, or in any particular order. Moreover, various activities described with respect to the methods identified herein can be executed in serial or parallel fashion. Although "End" blocks are shown in the flowcharts, the methods may be performed continuously. The Abstract of the Disclosure is provided to comply with 37 C.F.R. § 1.72(b), requiring an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter may lie in less than all features of a single disclosed embodiment. Thus, the following claims are hereby incorporated into the Detailed Description, with each claim standing on its own as a separate embodiment.

What is claimed is:

1. A system comprising:
a mobile electronic device comprising an image capture device configured to capture a digital image;
a database configured to store reminder data and a patient messaging configuration; and
a processor configured to (a) identify a patient, (b) identify a drug associated with the patient, (c) determine a reminder time schedule associated with a drug treatment plan of the patient including a reminder criterion that indicates a time at which the drug should be used by the patient, (d) access reminder data associated with the drug treatment plan of the patient based on identification of the patient, the reminder time schedule associated with the drug treatment plan of the patient, and the identification of the drug, (e) access the patient messaging configuration in the database based on the identification of the patient, (f) process the reminder data to determine a reminder time indicia that reflects a timing when the mobile electronic device should receive a notification, (g) compare the reminder time indicia against a time associated with the reminder criterion, (h) in response to determining that the reminder time indicia matches the reminder criterion, generate the notification reminding the patient to use the drug and transmit the notification to the mobile electronic device over a network according to the patient messaging configuration, (i) transmit a request to the mobile electronic device requesting that the patient capture the digital image of a drug label using the image capture device, (j) receive the digital image of the drug label from the mobile electronic device over the network, (k) decode the digital image of the drug label to determine a drug name based on the drug label by analyzing a text string on the drug label, (l) determine whether the drug name matches the drug, (m) transmit an authorization message to the mobile electronic device authorizing the patient to use the drug captured in the digital image when the drug name matches the drug, and (n) receive a message from the mobile electronic device indicating and verifying that the patient used the drug in accordance with the drug treatment plan.

2. The system of claim 1, wherein the reminder data further includes drug identifying indicia that identifies the drug, and wherein the processor is further configured to generate the notification based on the determination that the reminder criterion has been met, the patient messaging configuration, and the drug identifying indicia.

3. The system of claim 1, wherein the processor is further configured to identify the mobile electronic device as being associated with the patient,
wherein transmission of the notification is based on the identification of the mobile electronic device.

4. The system of claim 1, wherein the processor is further configured to receive a second digital image comprising a second drug label and determine that the second drug label corresponds to the drug using the second digital image of the second drug label, wherein generation of the notification is based on the determination that the reminder criterion has been met, the patient messaging configuration, and a determination that the second drug label corresponds to the drug.

5. The system of claim 1, wherein the verification is received through a user interface on the mobile electronic device.

6. The system of claim 1, wherein the verification of the use is received from the mobile electronic device, wherein the processor is further configured to compare the verification of the use with the reminder criterion to determine an amount of deviation, and dynamically adjust the reminder time indicia based upon the amount of deviation from the reminder criterion.

7. The system of claim 1, wherein the processor is further configured to access a scheduling calendar associated with the patient on the mobile electronic device, identify a scheduling conflict within the scheduling calendar based on the reminder time indicia, and adjust the reminder time indicia to an alternate time based upon the identification of the scheduling conflict.

8. The system of claim 1, wherein the notification includes a patient reminder to take a dose of the drug.

9. The system of claim 1, wherein the patient messaging configuration identifies a preferred patient delivery channel, a preferred patient delivery type, a preferred patient delivery person, or combinations thereof.

10. The system of claim 1, wherein the drug label includes a pharmacy prescription label.

11. The system of claim 1, wherein the reminder time indicia comprises a time associated with the mobile electronic device, and wherein the processor is further configured to compare the reminder criterion to the time associated with the mobile electronic device.

12. The system of claim 11, wherein the time associated with the mobile electronic device comprises a current time, a time zone in which the mobile electronic device is located, or an absolute time.

* * * * *